(12) United States Patent
Ostapenko

(10) Patent No.: US 8,528,407 B2
(45) Date of Patent: Sep. 10, 2013

(54) METHOD AND APPARATUS FOR IN-LINE QUALITY CONTROL OF WAFERS

(76) Inventor: Sergei Ostapenko, Wesley Chapel, FL (US)

( * ) Notice: Subject to any disclaimer, the term of this patent is extended or adjusted under 35 U.S.C. 154(b) by 405 days.

(21) Appl. No.: 12/449,948

(22) PCT Filed: Mar. 8, 2008

(86) PCT No.: PCT/US2008/056347
§ 371 (c)(1),
(2), (4) Date: Sep. 4, 2009

(87) PCT Pub. No.: WO2008/112597
PCT Pub. Date: Sep. 18, 2008

(65) Prior Publication Data
US 2010/0138027 A1   Jun. 3, 2010

Related U.S. Application Data

(60) Provisional application No. 60/894,196, filed on Mar. 10, 2007.

(51) Int. Cl.
*G01N 29/00* (2006.01)
*G01N 29/04* (2006.01)
*G01M 7/00* (2006.01)

(52) U.S. Cl.
USPC ............... 73/579; 73/12.01; 73/600; 73/602

(58) Field of Classification Search
USPC ............... 73/579, 593, 643, 599, 600, 602, 73/12.01; 702/84, 81, 82
See application file for complete search history.

(56) References Cited

U.S. PATENT DOCUMENTS

| | | | |
|---|---|---|---|
| 4,776,745 A | 10/1988 | Foley | |
| 5,086,775 A * | 2/1992 | Parker et al. | 600/453 |
| 5,257,544 A | 11/1993 | Khuri-Yakub | |
| 5,431,055 A * | 7/1995 | Takata et al. | 73/618 |
| 5,520,052 A * | 5/1996 | Pechersky | 73/579 |
| 5,696,324 A * | 12/1997 | Tsuboi et al. | 73/579 |
| 5,777,891 A * | 7/1998 | Pagano et al. | 702/39 |
| 5,996,415 A * | 12/1999 | Stanke et al. | 73/597 |
| 6,002,989 A | 12/1999 | Shiba et al. | |
| 6,374,199 B1 * | 4/2002 | Sugimoto | 703/2 |
| 6,413,789 B2 | 7/2002 | Ostapenko | |

(Continued)

FOREIGN PATENT DOCUMENTS

WO    WO/2007/128060    11/2007

OTHER PUBLICATIONS

J. Wehlgemuth et al Conference Record of the 31st IEEE PV Conference (IEEE Cat No. 05CH37608), 2005, pp. 1023-1027.
M. C. Bhardwej "Principles and methods of ultrasonic characterization of materials" Advanced Ceramic Materials, 1 (1986) pp. 311-324.

(Continued)

*Primary Examiner* — Helen Kwok
(74) *Attorney, Agent, or Firm* — Frijouf, Rust & Pyle P.A.

(57) ABSTRACT

An apparatus and a method are disclosed for testing the quality of a wafer. The apparatus and a method comprise coupling a broad-band actuator to the wafer. Sweeping frequencies are connected to the broad-band actuator for vibrating the wafer. An acoustic sensor is coupled to the wafer for measuring a resonant frequency of the vibrating wafer. The measured resonant frequency of the vibrating wafer is compared with a reference resonant frequency to deterring the quality of the wafer.

20 Claims, 15 Drawing Sheets

(56) References Cited

U.S. PATENT DOCUMENTS

| | | | |
|---|---|---|---|
| 6,425,869 B1 * | 7/2002 | Rafter et al. | 600/458 |
| 6,848,295 B2 | 2/2005 | Auner et al. | |
| 6,880,379 B2 * | 4/2005 | Hedberg et al. | 73/12.01 |
| 6,936,837 B2 | 8/2005 | Yamada et al. | |
| 7,061,602 B2 * | 6/2006 | Hamamatsu et al. | 356/237.2 |
| 7,141,440 B2 * | 11/2006 | Borden et al. | 438/5 |
| 7,356,377 B2 * | 4/2008 | Schwarm | 700/108 |
| 7,383,732 B2 * | 6/2008 | Okumura et al. | 73/602 |

OTHER PUBLICATIONS

E. Rueland et al, Proceedings oo 20th EU PVSEC (Barcelona, 2005) pp. 3242-3245.
T. Trupke et al Applied Physics Letters (2006), vol. 89, Issue 4, p. 044107.
T. Fuyuki et al Appl. Phys. Letters (2005), vol. 86, 262108.
J.P. Rakotoniaina et al, Proceedings of PV Solar conference (Paris, Jun. 2004), pp. 640-643.
A. Belyaev et al, Appl. Phys. Letters (2006) vol. 88, p. 111907.

* cited by examiner

Fig. 6
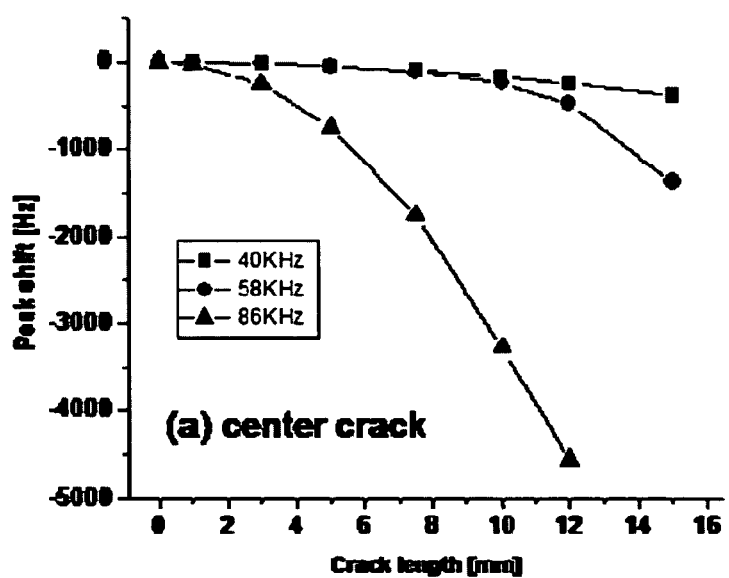
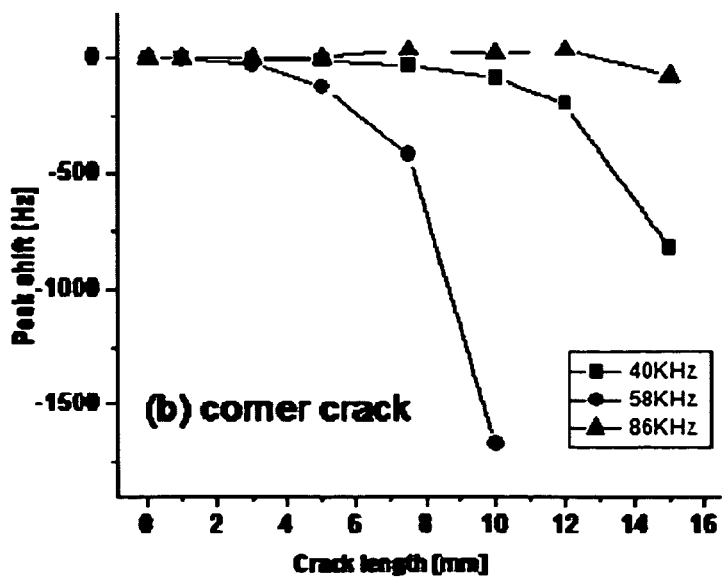

Fig.8
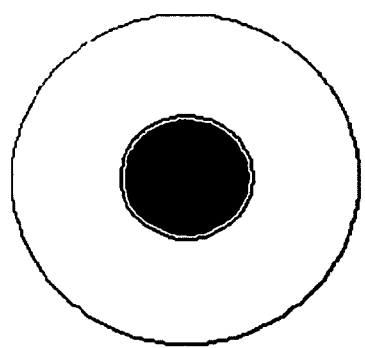
(a)
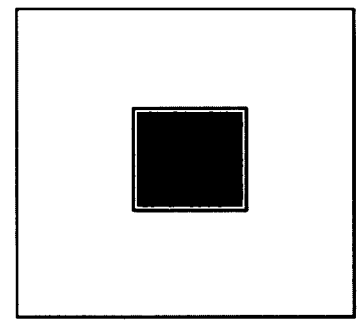
(b)
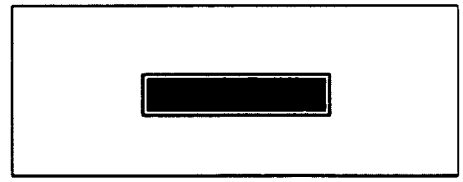
(c)

Fig.10
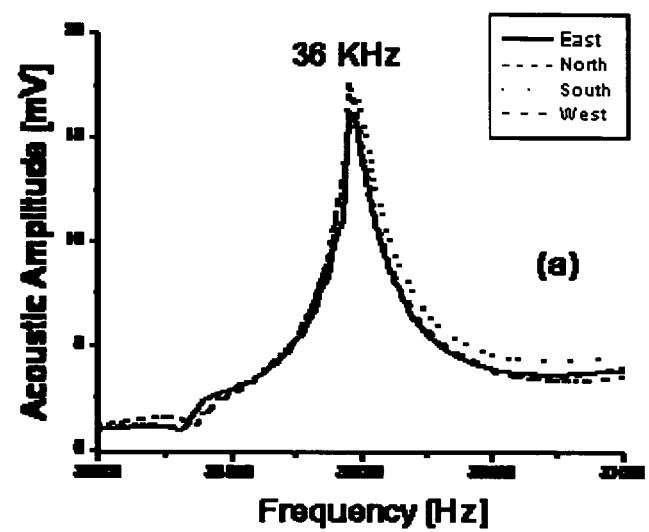
(a)
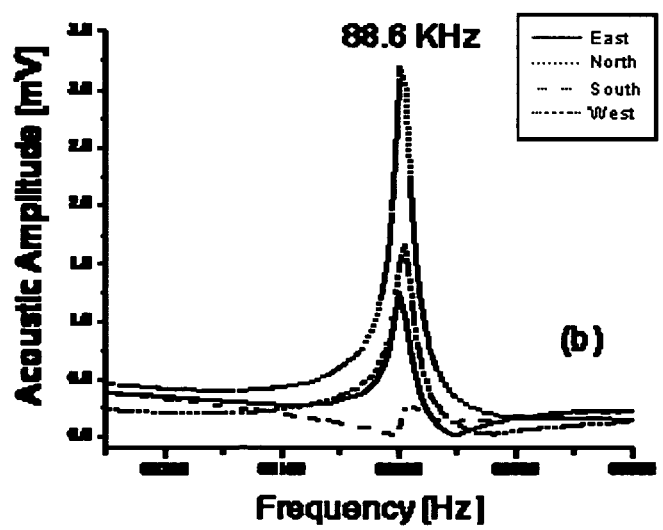
(b)

METHOD AND APPARATUS FOR IN-LINE QUALITY CONTROL OF WAFERS

CROSS-REFERENCE TO RELATED APPLICATIONS

This application is a 371 of Patent Cooperation Treaty application PCT/US2008/056347 filed Mar. 8, 2008 which claims benefit of U.S. Provisional Application 60/894,196 filed Mar. 10, 2007.

TECHNICAL FIELD

The invention relates broadly to methods and apparatus employed in the manufacture of devices based on wafers.

Examples of such devices include photovoltaic cells, light emitting devices and integrated circuits.

More particularly, the invention relates to apparatus and methods for in-line quality control of wafers, such as the quality control in conveyer type high throughput manufacture of silicon solar cells.

Whilst this invention has initially been developed for application to photovoltaic cells (and is described herein as such), the invention is not limited to this field.

BACKGROUND OF THE INVENTION

Any discussion of the prior art throughout the specification should in no way be considered as an admission that such prior art is widely known or forms part of the common knowledge in the field.

State-of-the-art silicon solar cell production is based on highly automated belt-type conveyor configurations. The as-cut p-type Si wafer is typically first subjected to chemical etching which removes saw damaged layers from both front and back surfaces of the wafer or edge damage from the laser cutting of silicon ribbons and then passes through the consecutive process steps including phosphorous diffusion to form a p/n junction; the deposition and firing of an antireflection $Si_3N_4$ coating; the creation of the front-side metal contact grid and Al back-side metal contact. Other modifications to optimize the process are also used in variants of these solar cell process steps. Finally, the individual solar cells are connected sequentially in strings, to achieve required voltage and current, and the strings are laminated into solar panels.

The PV industry, with crystalline silicon as a dominant segment, is rapidly expanding to meet growing renewable energy demands all over the world. The silicon wafer is a major contributor to the overall cost of the solar cell: currently up to 75% of the overall cost. One of the major technological problems is the identification and elimination of sources of wafers' mechanical defects such as thermo-elastic stresses and cracks leading to the loss of wafer integrity and ultimately to the breakage of as-grown and processed Si wafers and of PV cell based on these wafers.

The price of silicon raw material has grown substantially in the last three years due to a world-wide shortage of polycrystalline silicon feedstock. To compensate for the feedstock shortage, solar Si wafers are sliced thinner to a thickness of less than 100 microns [J. Wohlgemuth, M. Narayanan, R. Clark, T. Koval, S. Roncin, M. Bennett, D. Cunningham, D. Amin, J. Creager "*Large-scale PV module manufacturing using ultra-thin polycrystalline silicon solar cells*" *Conference Record of the Thirty-First IEEE Photovoltaic Specialist Conference* (IEEE Cat. No. 05CH37608), 2005, Pages 1023-1026]. Wafer areas have also been increased to reduce overall production costs, and larger sizes, up to 210 mm×210 mm, are now available.

Thinner and larger wafers are, however, more difficult to handle during production, this leads to a reduction in yield due to increased breakage especially in high speed automated manufacture. In-line wafer breakage reduces equipment throughput as a result of down time required for cleaning in-line equipment, and removing broken wafers from fixtures.

There is, therefore, a recognized need for devices and a methodology for fast in-line quality control methods and apparatus. Common problem leading to wafer breakage is related to small cracks that under thermal or mechanical stress cause wafer's mechanical fracture. Further, it is recognised that impact of a particular crack on wafer's mechanical property depends on the size of the crack and its location within the wafer.

The majority of the methods presented in the prior art are based on imaging techniques, comprising capturing and processing an image of a wafer in order to determine its spatial irregularities.

Scanning Acoustic Microscopy (SAM) is an imaging technique using 150 MHz pulses for precise identification and visualization of micro-cracks as small as 10 microns. The cracks are identified as acoustic impedance discontinuity of wafer at the crack region [M. C. Bhardwaj "*Principles and methods of ultrasonic characterization of materials*" *Advanced ceramic materials*, 1 (1986) pp 311-324]. The steps of SAM technique including, immersion of wafer into de-ionized water, mapping of the pulse amplitude, and data analyses are each relatively slow, so that the full testing procedure even in its automated version can occupy several minutes of precious manufacturing time. This evidently makes SAM unsuitable for in-line applications where no more than a few seconds per wafer is acceptable for quality inspection.

Another approach is offered by an optical inspection imaging where relatively large cracks are visualized by a light transmission technique [E. Rueland, A. Herguth, A. Trummer, S. Wansleben, P. Fath "*Optical micro-crack detection in combination with stability testing for in-line-inspection of wafers and cells*", *Proceedings of 20th EU PVSEC* (Barcelona, 2005) pp. 3242-3245]. This technique, however, lacks the capability to observe small cracks at the wafer's periphery. The optical inspection is also non-applicable to processed wafers having back-side Al contact and to complete solar cells. An additional limitation of the transmission technique is that tightly closed cracks with width of ~1 micron are not detectable due to the optical diffraction limit.

Recently reported data on luminescence imaging [T. Trupke, R. A. Bardos, M. C. Schubert, W. Warta, "*Photoluminescence imaging of silicon wafers*", *Applied Physics Letters* (2006), Volume 89, Issue 4, 44107; T. Fuyuki, H. Kondo, T. Yamazaki, Yu. Takahashi, Yu. Uraoka "*Photographic surveying of minority carrier diffusion length in polycrystalline silicon solar cells by electroluminescence*" *Appl. Phys. Letters* 86, 262108 (2005)] is particularly developed for testing of indirect band-gap semiconductor devices such as silicon solar cells. As an imaging technique the method's speed is limited by implemented image recognition software, which needs to perform a substantial computational task of analysing complex luminescence image of a wafer. Another drawback of the method is that other defects such as surface scratches and dislocation slip lines can be misinterpreted as cracks thus leading to false positive answers. The application of this method to identification of electrically isolated or poorly connected regions such as those caused by breaks in the metal pattern was disclosed in details in an international patent application PCT/AU2007/000595.

Ultrasonic lock-in thermography is sufficiently sensitive, however it requires a longer measuring period for signal averaging due to low infrared intensity [J. P Rakotoniaina, O. Breitenstein, M. H. Al Rifai, D. Franke, A. Schnieder "*Detection of cracks on silicon wafers and solar cells by lock-in ultrasound thermography*", Proceedings of PV Solar conference (Paris, June 2004), pp. 640-643].

A new non-imaging experimental algorithm for fast crack control using Resonance Ultrasonic Vibrations (RUV) was disclosed in the paper [A. Belyaev, O. Polupan, W. Dallas, S. Ostapenko, D. Hess, J. Wohlgemuth "Crack detection and analyses using resonance ultrasonic vibrations in full-size crystalline silicon wafers", Appl. Phys. Letters 88, 111907-1 (2006). The RUV approach for stress control in silicon wafers was also disclosed in the U.S. Pat. No. 6,413,789 B2 [S. Ostapenko "Method of detection and monitoring stresses in a semiconductor wafer" U.S. Pat. No. 6,413,789 B2]. The method, as described in prior publications, allows for fast detection of wafer's imperfections but is not applicable for in-line control. The method involves measurement of a single resonant curve and correlating one parameter of the curve with the internal stresses or cracks in a wafer. The wafers, however, vary in a range of physical parameters such as lateral dimensions, thickness, and shapes. While small variations of these parameters are acceptable within the quality requirements for PV cells, these variations often lead to false positive events when an acceptable wafer is falsely recognised as a potentially breakable wafer with cracks. Further, the method is not capable to provide an information in relation to the location of crack. Above mentioned shortcoming limit benefits of using the method of U.S. Pat. No. 6,413,789 for in-line quality control of wafers.

Another method, based on impact testing is disclosed in the U.S. Pat. No. 5,257,544 titled "Resonant frequency method for bearing ball inspection". This invention provides a method for detecting defects in test objects which includes generating expansion inducing energy focused upon the test object at a first location, thereby causing pressure wave within the test object. At a second location, the acoustic waves are detected and the resonant frequencies' quality factors are calculated and compared to predetermined quality factor data. The inventors claim that such comparison provides information of whether the test object contains a defect. Once again, the method operates with a single rejection parameter, which, when applied to wafers, limits its ability to distinguish cracked samples from statistically variable samples, leading, therefore to high proportion of false positive event unacceptable in manufacturing practice. Further the method requires high precision in locating an incoming acoustic pulse (impact) and of a sensor detecting acoustic waves. This precludes identification of cracks located in proximity to the selected positions. Crucially, an impact testing by a single or multiple acoustic pulses is less sensitive than techniques based on periodical sinusoidal excitation. The periodic excitation allows for substantial reduction of signal-to-noise ratio by synchronizing frequency and phase of a detected response to an excitation with that of a reference signal causing the excitation. Furthermore, the impact testing has high probability to creating new cracks in standard silicon wafers when focused ultrasonic beam hit the wafer close to areas of high internal stress.

It is an object of the present invention to overcome or ameliorate at least one of the disadvantages of the prior art, or to provide a useful alternative.

Therefore, the present invention addresses the need for fast, accurate and non-destructive determination of mechanical defects in wafers, including detecting and locating cracks in wafers, particularly applicable as a diagnostic in-line tool in solar cell production.

SUMMARY OF THE INVENTION

The invention provides a method and apparatus for in-line detection and location of cracks in a thin wafer by exciting multiple mechanical vibrations in the wafer and measuring the response of the wafer at certain selected locations.

In its broadest aspect the present invention presents a method for in-line mechanical quality control of wafers, said method comprises the steps of:
  coupling a wafer with a broad-band actuator,
  providing at least one acoustic sensor adapted for measuring vibrations at selected locations on the wafer,
  measuring multiple resonant frequency curves by sweeping frequency of the broad-band actuator simultaneously in predetermined frequency intervals and recording the wafer's resonance vibrations using the acoustic sensor;
  comparing the measured resonant frequency curves with reference resonant frequency curves,
  generating a rejection signal if the deviation between measured and reference resonant frequency curves exceeds a defined set of values, and
  decoupling the wafer and the actuator.

In a preferred embodiment a resonance frequency, an amplitude and a bandwidth of each of the resonant curves are each compared with that of a reference resonance frequency curves.

In one embodiment according to this aspect of the invention, the method for in-line mechanical quality control of wafers is calibrated using a standard wafer. The standard wafer is carefully selected to be mechanically sound and crack free. The standard wafer is typically inspected using a range of the characterization methods known in the art, but not necessarily suitable for the requirements of fast in-line quality control.

The calibration of the method for in-line control of wafers includes the steps of:
  Recording of a full range acoustic frequency spectrum of the reference wafer;
  Analysis of the spectrum, identification of resonance peaks and selection of those peaks that are sensitive for cracks and other mechanical defects that can cause the breakage of a wafer;
  Selection of the required number and positions of the sensors, depending on the quality requirements of the manufacturing process that is to be controlled. While we found that in most cases two separate sensors provide sufficient data, it is appreciated that the tougher the requirements for quality the larger the number of sensors required;
  Including a quality table of acceptable deviations into the defined set of values.

It is preferable to use a plurality of standard wafers to record statistical variations of the reference resonant curves caused by the factors not leading to breakage during high throughput manufacturing process. Such factors include, for example, small variations in lateral dimensions of wafer, its thickness, and shape. In some cases some small cracks are considered acceptable, especially when these cracks are located in non-critical parts of wafers. Therefore, it is preferable that plurality of standard wafers is selected to be representative in respect to a full batch excluding, of course, cracks that lead to the mechanical breakage. During the calibration each of the standard wafers is subjected to the same procedural steps as the tested wafer during in-line testing within a continuous manufacturing process. This excludes the step of comparing the resonant frequency curves and the step of generating the rejection signal.

In one embodiment, the statistical analysis of the reference resonant frequency curves comprises determination of statistical parameters listed in the following table.

TABLE 1

Statistical parameters of reference resonant frequency curves.

|  | Frequency of a resonance | Amplitude | Bandwidth |
| --- | --- | --- | --- |
| A parameter of resonance curve of the i-th frequency interval | $f_i$ | $A_i$ | $BW_i$ |
| Corresponding mean value determined from the standard frequency curves | $\bar{f}_i$ | $\bar{A}_i$ | $\overline{BW}_i$ |
| Standard deviation of the mean value | $\sigma_i^f$ | $\sigma_i^A$ | $\sigma_i^{BW}$ |
| Sensitivity factor | $n_i^f$ | $n_i^A$ | $n_i^{BW}$ |

In a preferred embodiment each of the multiple resonant frequency curves is analyzed to compute the parameters shown in the first raw of the table. The rejection signal is generated when the following conditions are simultaneously satisfied:

$$|f_i - \bar{f}_i| > n_i^f \sigma_i^f$$

$$|A_i - \bar{A}_i| > n_i^A \sigma_i^A$$

$$|BW_i - \overline{BW}_i| > n_i^{BW} \sigma_i^{BW}$$

The coefficients $n_i$ are chosen in accordance with a selected detection limit and with an acceptable number of false rejections. It is appreciated that the lower the detection limit the higher the number of false rejects. The invention provides for adjusting the coefficients $n_i$ depending on specific requirements of a particular manufacturing process. The detection limit is preferably the minimum size of a crack which, if detected in a wafer, causes generation of the rejection signal.

In a further embodiment, prior to coupling with the actuator and after completion of the measurements, the wafer progresses through a manufacturing line; the manufacturing line usually comprises a number of manufacturing processes.

In a typical arrangement, the manufacturing line includes a movable platform, conveyer belt, pick-and-place mechanisms or any other transportation means used in such continuous manufacturing processes, and the wafer is engaged with the transportation means.

The wafer coupled with the actuator is preferably disengaged from the transportation means.

In a still further embodiment the coupling and decoupling the wafer and the actuator is synchronized with the operation of the transportation means. It is essential to achieve an in-line integration of the quality testing procedure. In one example, the transportation means remain motionless during the recording of the resonant frequency curves. In another example, the movement of the transportation means just slows down. It is preferable that when the recording and analysis of the resonant frequency curve is completed and the wafer is about to be decoupled from the actuator, the next subsequent wafer is in proximity to the actuator, so that the in-line quality control procedure can be applied to the next wafer without undue delay.

In a yet further embodiment the coupling of the wafer and the actuator is achieved by a high speed electronically controlled coupling means such as electrostatic chuck, utilizing electrostatic attraction, magnetic coupling, injecting a coupling fluid, or any other coupling means known in the art of acoustic measurements. In a preferred arrangement the coupling means is an electronically controlled vacuum switch creating a vacuum in the space between the wafer and the actuator so that the wafer is coupled with the actuator by action of vacuum force.

Typically the actuator comprises a piezoelectric generator of acoustic wave and a body on which the generator is mounted. The invention provides for an arrangement where the wafer coupled with the actuator is mechanically supported by the actuator during the measurement of the resonant frequency curves. In one realization the wafer rests on the actuator. In another arrangement the wafer is suspended beneath the actuator.

In another embodiment, the rejection signal initiates transferring of the wafer to the separating means. In the absence of the rejection signal the accepted wafer is either returned to the transportation means, from which it was disengaged prior to the measurements or is moved to another transportation means. In both cases the transportation means transfer the wafer through stages of a manufacturing process. If, however, the wafer was determined to be not suitable for further stages of manufacture, it is transferred to the separation means. Similarly to the transportation means, the separation means may comprise a conveyer belt, a pick-and-place mechanism, movable platform, or even a stack or a cassette where the rejected wafers are collected.

To minimize false positive decisions when an acceptable wafer is mistakenly transferred to the separation means, the invention provides for an additional step of inspecting the rejected wafer. It is appreciated that only a small proportion of the wafers will be rejected and, therefore, the step of inspecting the rejected wafer does not need to satisfy stringent requirements of in-line procedures, such as fast handling and short duration of time intervals required for collection and processing of data. The inspection of the rejected wafer preferably comprises an imaging technique, such as, for example, luminescence.

In a still another embodiment, if the inspection of the rejected wafer determines that the reject signal was false, the wafer is returned to the transportation means and the statistical parameters, including the defined set of values, are adjusted to accommodate the new reference information.

In a yet another embodiment vibrations of the wafer are simultaneously detected in at least two differing selected positions of the wafer by at least two separate acoustic sensors. The sensors may be in a contact with the wafer at selected locations or alternatively may be placed proximate the selected positions. In the latter case the wafer's vibrations can be detected by one of the known means including, for example, monitoring the position or the direction of a reflected laser beam. It is preferable to choose the selected positions on the wafer's periphery.

In some cases, in particular, when a decision to accept/reject the wafer is on the boundary of accept/reject conditions the method may include relocating the sensors to new selected positions and repeating the measurements of the resonant frequency curves.

From another aspect, the invention provides an apparatus for in-line quality control of wafers comprising:

A broad band acoustic actuator capable of exciting mechanical vibrations in a wafer simultaneously in the predetermined frequency ranges.

At least one acoustic sensor capable for detecting mechanical vibrations in the wafer and converting the vibrations into electrical signals At least two electrical generators jointly delivering the superposition of the electrical signals to the acoustic actuator At least two electrical amplifiers each synchronized with the corresponding electrical generator and tuned to measure the vibrations of the wafer in one of the predetermined frequency ranges Data acquisition and control system and A means for fast coupling the wafer with the actuator.

In one embodiment, the apparatus further comprises a transportation means for transferring the wafer prior to coupling the wafer and the actuator. The transportation means is preferably adapted to disengage the wafer for the measurement of the resonant frequency curves.

In another embodiment, the data acquisition and control system is adapted to synchronize the transportation means with the means for fast coupling the wafer and the actuator.

In yet another embodiment, the apparatus further includes a means for positioning the sensors at the selected locations of the wafer.

In a further embodiment, the apparatus further includes the means for fast coupling the wafer and the actuator. The means for fast coupling the wafer and the actuator preferably comprises a fast electronically controlled vacuum switch, so that the wafer is mechanically coupled with the actuator by the action of a pressure differential created between the outer side of the wafer facing the atmosphere, and the inner side facing the actuator. In one realization, the pressure differential is applied to the wafer through a small hole created in the actuator.

After the resonant frequency curves are detected, the wafer may be uncoupled from the actuator and returned to the manufacturing line. This is commonly achieved by returning the wafer to the transportation means.

However, if the wafer fails quality requirements and is found to be not suitable for further manufacturing steps, the wafer may be removed from the processing line and, for example, placed in the separation means designated for reworking or disposal.

In an alternative arrangement, the wafer is in a stack of wafers and is taken from the stack for coupling with the actuator. If the wafer complies with the quality requirements it may be returned to the original stack, placed into another stack or transferred onto the transportation means. If, however, the wafer fails the quality requirements, it may be, for example, transferred to a container or yet another stack designated for reworking or disposal.

Based on the decision on the quality of the wafer an electrical signal may be generated to either keep the wafer within the manufacturing line or to remove the wafer from the manufacturing line.

BRIEF DESCRIPTION OF THE DRAWINGS

Other advantages of the present invention will be readily appreciated as it becomes better understood by referring to the following detailed description when considering the accompanying drawings wherein:

FIG. 6 is a dependence of peak-shift, at selected frequencies, on the size of a crack according to the sixth example of the invention.

FIG. 8 demonstrates commonly used shapes of wafers and corresponding shapes of the actuators according to the eights example of the invention.

FIG. 10 depicts resonance peaks obtained from measurements made at the four sides of a square wafer according to the $10^{th}$ example of the invention.

DETAILED DESCRIPTION OF THE INVENTION

Figure 1:
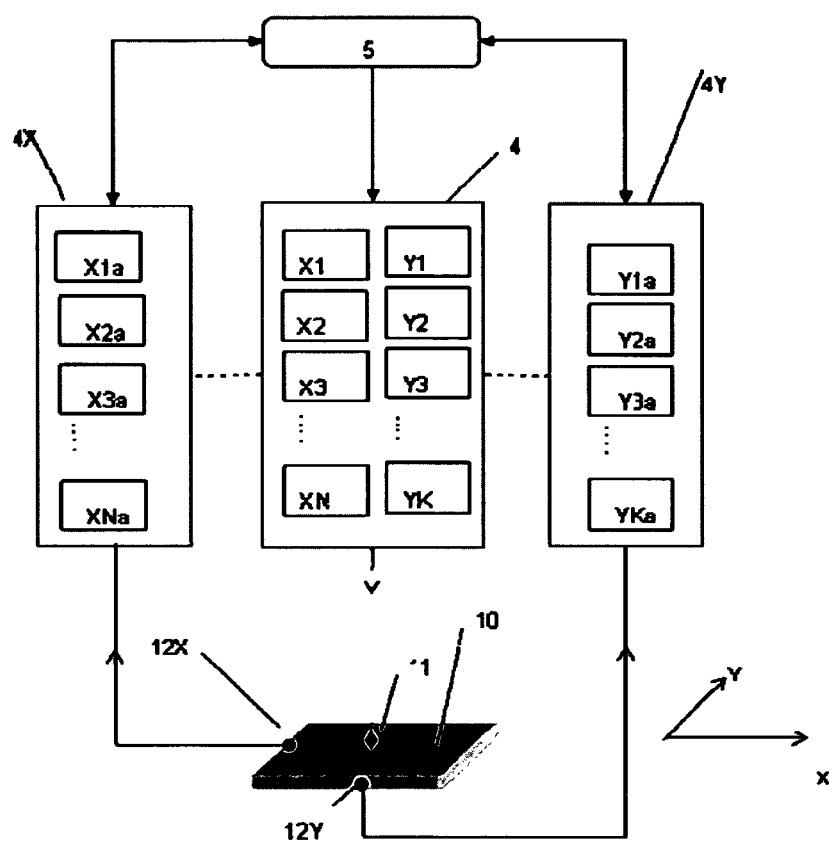
FIG. 1 is a diagram showing a method for quality control of wafers according to the first example of the invention.

The chosen first example of the invention, shown in FIG. 1 includes a generator subsystems 4 comprising a number of generators X1, X2, . . . XN, Y1, Y2 . . . YK, each tuned to a certain frequency range and each controlled by a data acquisition and control subsystem. Each of the generators is synchronized with a corresponding amplifier either from a subsystem 4X connected to a sensor 12X, which detects vibrations of a wafer 10 in the X-direction, or from a subsystem 4Y, connected to a sensor 12Y, which detects vibrations of the wafer 10 in the Y-direction.

It is common for the predetermined frequency range of X-generators to be similar or even identical to that of the analogues Y-generators, such that the generators X1 and Y1 may operate in the same range of frequencies. However, each of the X-generators operates in a different frequency range. The number of generators depends on the number of resonance peaks to be recorded. The number N of X-generators is not necessarily the same as the number K of Y-generators.

The generators 4 are electrically connected to an actuator 11 that is acoustically coupled to a wafer 10. The actuator and the sensors are typically piezoelectric devices. The actuator is a linear device, so that a superposition (linear combination) of independent electrical signals generated by X- and Y-generators is converted by the actuator to a superposition (linear combination) of acoustic vibrations at frequencies identical to frequencies of the independent electrical signals superimposed by the actuator.

In operation, a data acquisition and control subsystem 5 effects the generators 4 to sweep the frequency of generated electrical voltage in a range predetermined for each generator. This causes the actuator 11 to vibrate according to a superposition of signals created by the generators. The actuator 11, in turn, causes ultrasonic vibrations in the wafer 10. The vibrations are measured by the sensors 12X and 12Y and further amplified by the amplifiers 4X and 4Y for acquisition by the data acquisition and control subsystem 5. In this way, individual frequency sweeps from each generator are transferred to corresponding vibration modes of the wafer and these vibration modes are recorded independently from each other and simultaneously by the sensors 12X and 12Y.

Figure 2:
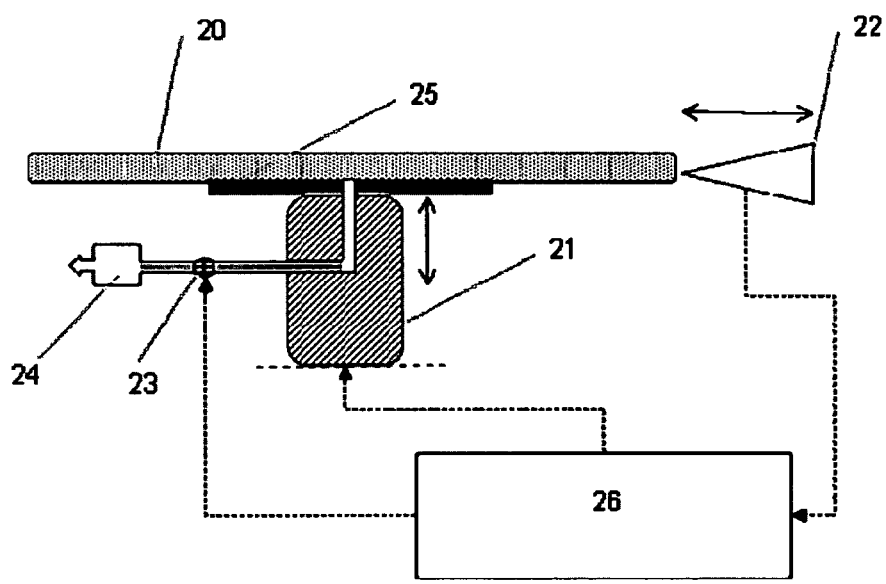
FIG. 2 is a diagrammatic cross-sectional representation of an apparatus for in-line mechanical quality control of wafers according to the second example of the invention.

An apparatus for in-line mechanical quality control of wafers of the second example, shown schematically in FIG. 2, comprises a vacuum holder 21; a piezoelectric actuator 25, supported by the vacuum holder 21 and acoustically coupled to a wafer 20; a sensor 22, also acoustically coupled to the periphery of the wafer 20; a vacuum pump 24; an electronically controlled vacuum switch 23; and an electronic block 26, that includes a generator, an amplifier, and a data acquisition and control subsystem.

The actuator 25 has a small central hole allowing a reliable vacuum coupling between the wafer and the actuator by applying small (about 50 kPa) negative pressure to the back side of the wafer.

In operation, the vacuum pump 24 is switched on permanently and the vacuum switch 23 is initially in the closed position. When the wafer 20 is positioned on the actuator 25 the electronic block opens the vacuum switch 23 and the negative pressure created at the back side of the wafer 20 ensures coupling of the wafer 20 and the actuator 25. The sensor 22 approaches the wafer 20 and contacts the wafer's edge at a selected location. The electronic block immediately commences sweeping frequency simultaneously at a number of predetermined frequency ranges. The actuator 25 vibrates causing ultrasonic vibrations in the wafer 20; the sensor 22 converts these vibrations into electrical voltage that is in turn amplified, acquired and analyzed by the electronic block 26. By comparing the measured resonant frequency curves with reference resonant frequency curves the electronic block 26 makes a rejection-acceptance decision. When the measurements are completed, the electronic block 26 closes the vacuum switch 23; the wafer 20 can now be removed from the apparatus and depending on the rejection-acceptance decision either returned to the conveyer line for further processing or placed aside for reworking or disposal.

In a preferred arrangement, the wafer is on a transportation means, typically—on a conveyer belt (not shown), prior to coupling the wafer and the actuator. The transportation means may stop for a short time required for the measurement. Typically the transportation means has an opening and the wafer is transported in such a way that the opening is below and close to the centre of the wafer. The vacuum holder 21 supporting the actuator 25 is attached to a Z-stage (not shown) positioned bellow the transportation means. The Z-stage moves the vacuum holder 21 upwards until the actuator is in contact with the wafer. This is followed by opening the vacuum switch 23 to provide a pressure differential sufficient for acoustic coupling the actuator and the wafer. Optionally the Z-stage may further raise the vacuum holder 21 such that the wafer mechanically supported by the actuator is raised above the conveyer belt. The sensor 22 is now in contact with the wafer's edge. When the measurements are completed, the data acquisition and control system switches the vacuum switch off; this removes the pressure differential and decouples the wafer 20 and the actuator 25. Prior to that the system may cause the Z-stage to lower the wafer back to the conveyer belt. The vacuum holder 21 is then transferred to its position below the transportation means while the wafer 20 is returned to the transportation means. If, however, the rejection signal is generated, the wafer may be removed from the transportation means sideways. The transportation means recommences its movement until the next wafer is brought to a measurement position above the vacuum holder. The transportation means stops at this position and the measurements are now repeated with another wafer. In this way the in-line mechanical quality control of wafers is conducted.

A horizontal double-sided arrow in FIG. 2 shows directions of movement of the sensor 22 towards (before measurements) and away from (after measurements) the wafer 20, whereas a vertical double sided arrow shows the directions of movement of the actuator 25, attached to the vacuum holder 21, upwards towards the wafer 20 and then upwards with the wafer 20 (before the measurements); and downwards with the wafer 20, and, after the wafer 20 rests on the transportation means, further downwards bellow the transportation means (after the measurements).

Figure 3:
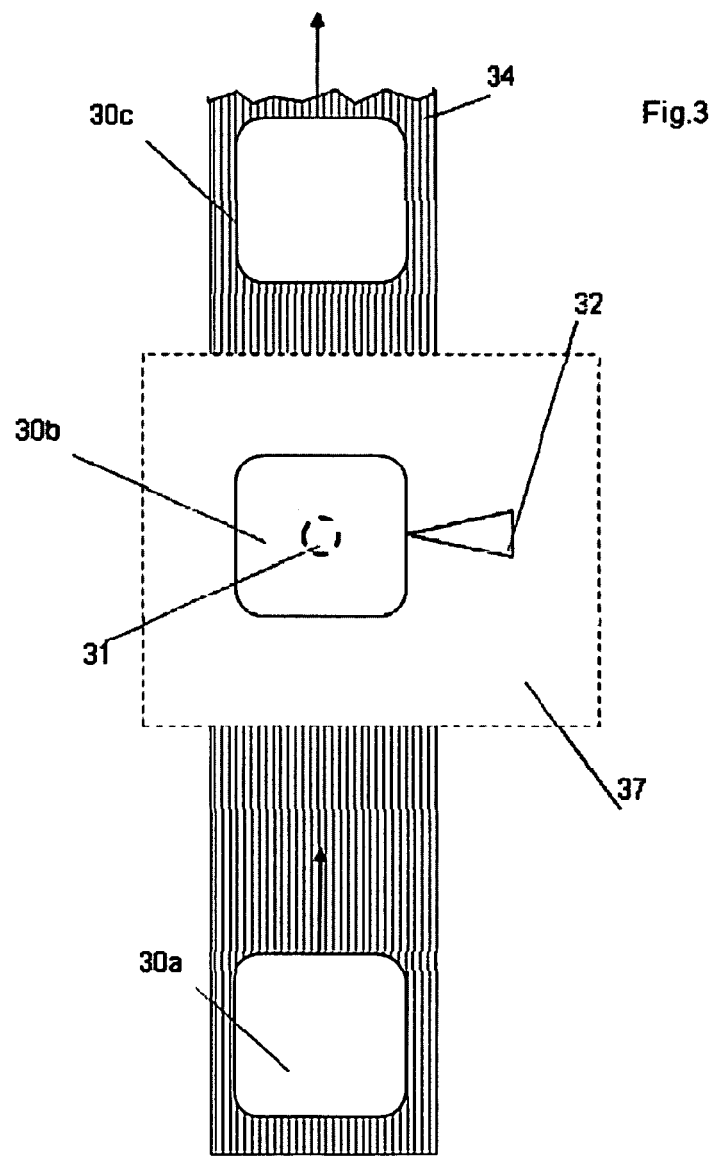
FIG. 3 is a diagrammatic top-view representation of a device for in-line mechanical quality control of wafers according to the third example of the invention.

An apparatus of the third example of the invention is shown in FIG. 3. A wafer 30 is shown in 3 separate positions: before the test (30*a*), during the test (30*b*), and after the test (30*c*). The wafer is transported by a conveyer belt 34. During the test the wafer enters the measuring unit 37, where it is acoustically coupled with an actuator 31 and a sensor 32. After completion of the test the wafer 30 is returned to the conveyer belt 34.

Figure 4:
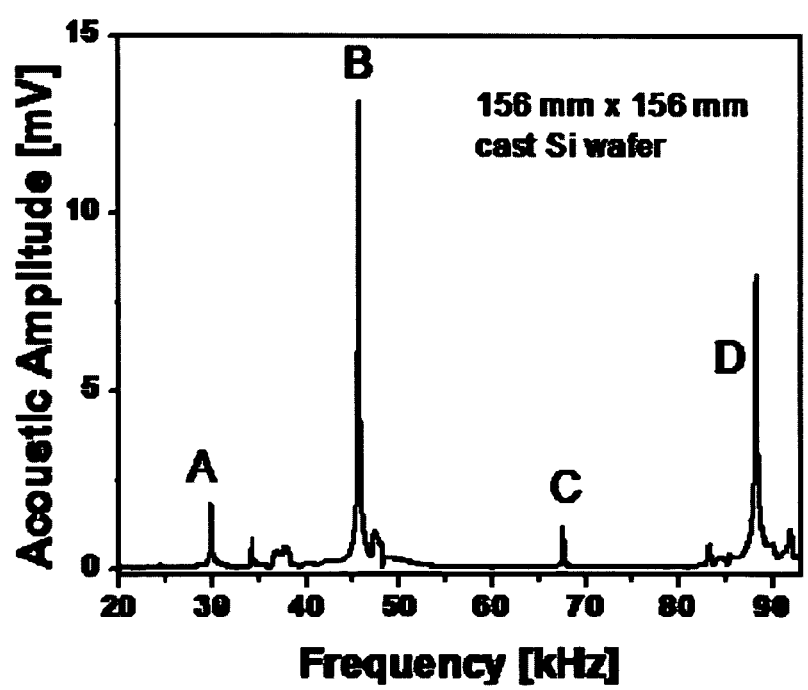
FIG. 4 is a full range ultrasonic frequency spectrum obtained on a crack-free reference wafer, showing four individual vibration modes A, B, C and D according to the fourth example of the invention.

FIG. 4 is a calibration frequency scan recorded on a crack-free standard wafer in the frequency range from 20 to 93 kHz. As shown, four separate resonance peaks, labeled as A, B, C and D, are recorded and selected for in-line mechanical quality control of wafers.

Figure 5:
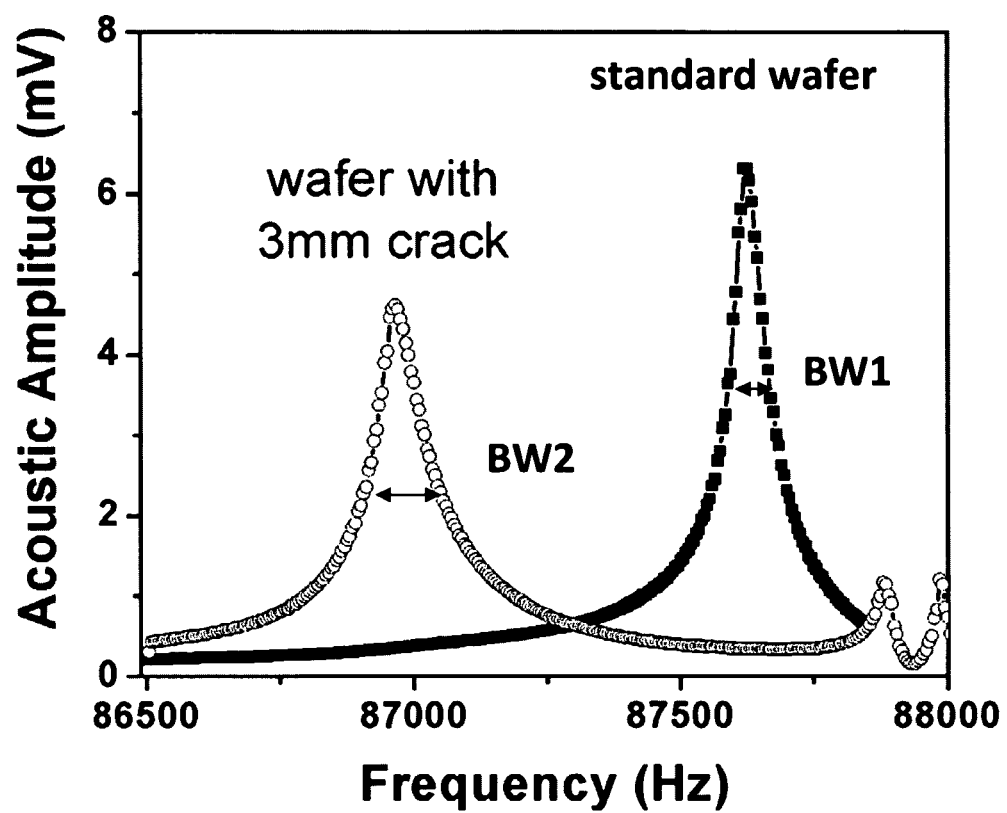
FIG. 5 is a comparison of the resonance frequency curves on the reference wafer and the wafer with a crack according to the fifth example of the invention.

FIG. 5 shows experimental verification of the invention. Two identical in size and shape 125 mm×125 mm square shaped single-crystal silicon wafers were tested. One of these wafers is a standard wafer (closed marks), having no mechanical or structural defects such as cracks, that was confirmed by Scanning Acoustic Microscopy imaging with 10 microns resolution. The second wafer (open marks) has a 3 mm peripheral crack introduced at the center of the wafer's edge. The effect of the crack is clearly observed as a downward frequency shift, reduction of the peak amplitude and increased peak bandwidth (peak broadening).

FIG. 6 demonstrates that in-line mechanical quality control of wafers is capable for detecting dimensions of cracks in a wafer and distinguishing between cracks at the centre of the wafer edge and that at its corner. In this example peak shifts (difference between the measured resonance frequency and the reference resonant frequency) measured at three different resonances (at 40 kHz, 58 kHz and 86 kHz) are presented as functions of the length of a crack. The example demonstrates that 86 kHz resonance is preferable for the detection of cracks close to the centre of the wafer's edge, whereas 58 kHz is more suitable for the detection of cracks positioned in the proximity of the wafer's corners. At least two separate resonances are therefore required to indicate the position of a crack on a wafer edge.

Figure 7:
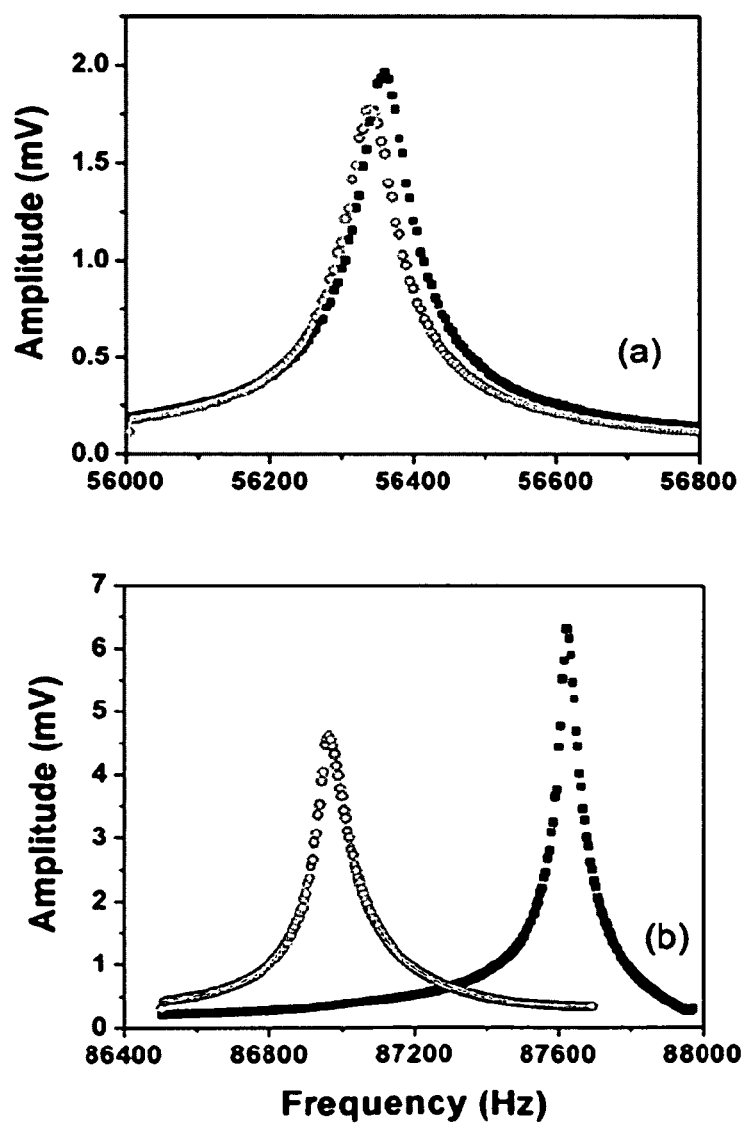
FIG. 7 demonstrates the effect on the position, shape and amplitude of the resonance peaks by cracks in a wafer according to the seventh example of the invention.

An example of FIG. 7 shows resonance peaks recorded for a standard wafer (closed marks) and a cracked wafer (open marks). A resonance at around 56.3 kHz is shown in FIG. 7*a*, and at around 87.6 kHz—in FIG. 7b. A 6 mm crack positioned closed to the centre of the wafer's edge resulted in a small 18 Hz frequency shift at the 56.3 kHz resonance, and in a substantial 600 Hz downward frequency shift at the 87.6 kHz resonance. The method for in-line mechanical quality control of wafers would reject this wafer from further processing.

Three different examples of actuators are shown in the FIG. 8. An arrangement when the shape of a transducer is similar to the shape of a wafer usually results in better acoustic matching and is preferred. A circular actuator is preferable for use with a circular wafer (FIG. 8 a), a square actuator—with a square wafer (FIG. 8b) and a rectangular actuator—with a rectangular wafer (FIG. 8c). FIG. 8 also demonstrates that in a preferable arrangement a transducer is coupled to the geometrical centre of a wafer.

Figure 9:
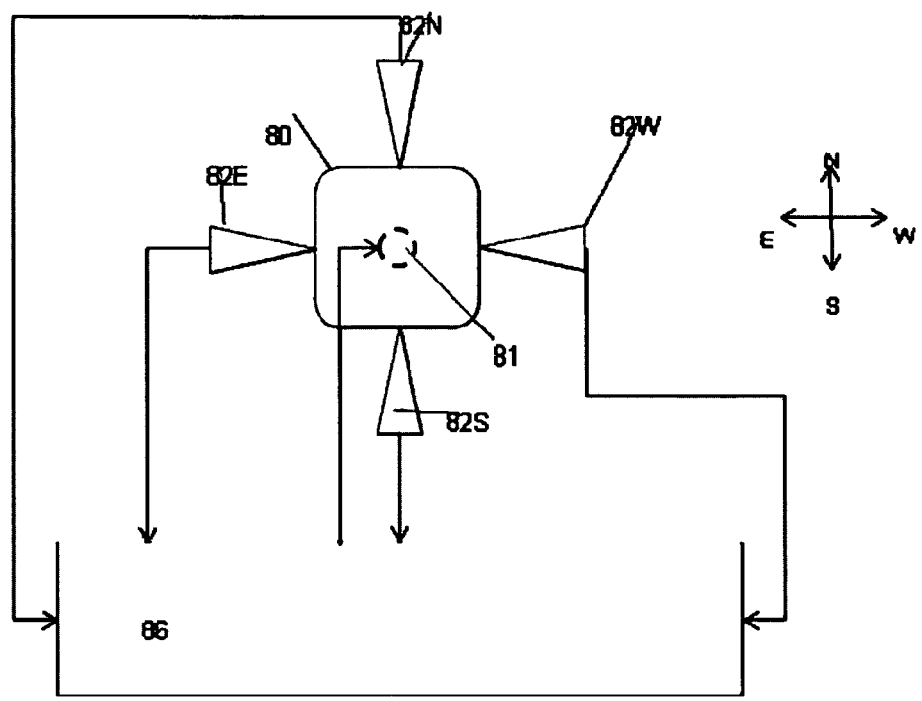
FIG. 9 is a diagrammatic representation of a four-sensor apparatus according to the $9^{th}$ example of the invention.

Yet another example of the invention is shown diagrammatically in FIG. 9. An apparatus of this example comprises four sensors 82, each adapted to measure mechanical vibration of a square wafer 30 at approximately the centre of each side of the square. The sensor 82N measures at the north side of the wafer, sensor 82S—at the south side and so on. An actuator 81, acoustically coupled to the wafer 80, is controlled by an electronic block 86. The electronic block 86 is adapted to sweep frequency in two independent intervals and to collect resonant frequency curves from four separate sensors. Therefore, the block 86 comprises two generators and two groups of amplifiers (four amplifiers in each group). Each amplifier from the first group is synchronized with the first generator to measure the first vibration resonance and, similarly, each amplifier from the second group is synchronized with the second generator to measure the second resonance.

In operation, the first and the second generators sweep the frequency around the first and the second resonance peaks correspondingly, causing vibration of the actuator, which in turn excites vibrations of the wafer. If the wafer is free of defects, the resonance peaks detected at each of N, S, W, E sides of the wafer are identical at each of the preselected resonances. If, however, one of the sides contains defects the resonance peak measured at that side may deviate from those measured at the other three sides of the wafer.

FIG. 10 shows data obtained experimentally by measuring two vibration resonances at each of four sides (N, S, W, E) of a 125 mm×125 mm square wafer. In FIG. 10 (a) a resonance peak at 36 kHz is measured at the centers of four different sides (East, North, South and West) of the wafer. All four resonance peaks have close values of amplitude, peak position and bandwidth.

In FIG. 10 (b) the same measurements were repeated at a different resonance peak of 88.6 kHz. Evidently, in this case the amplitude and shape of signals are quite different. The South side has the smallest resonance peak amplitude due to mechanical defects on this side. Therefore, method and apparatus of the invention allow not only to detect the presence of mechanical defects in a wafer, but also to determine their geometrical location.

Figure 11:
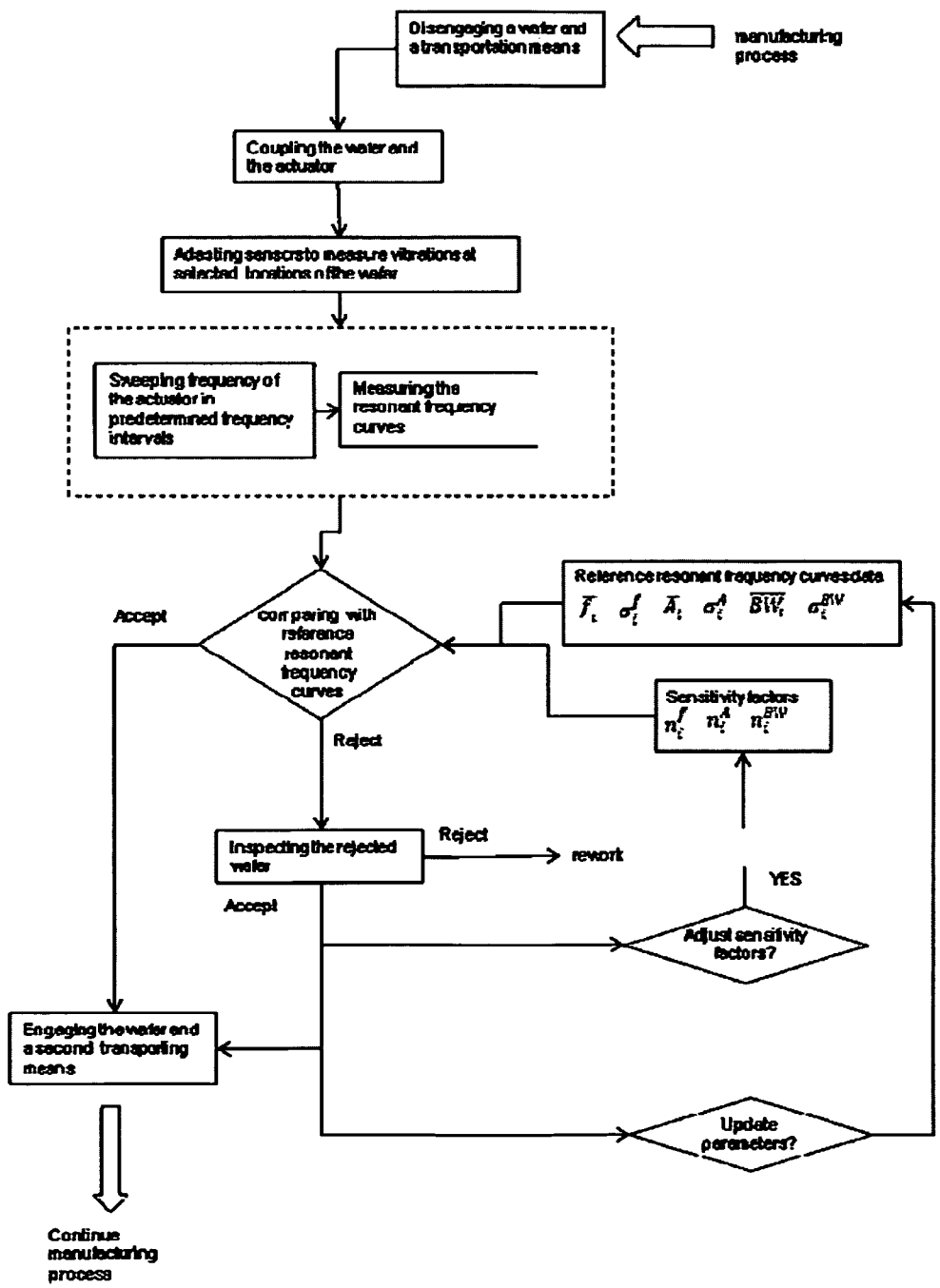
FIG. 11 is a flow-chart diagram of a method for quality control of wafer according to the $11^{th}$ example of the invention.
Figure 12:
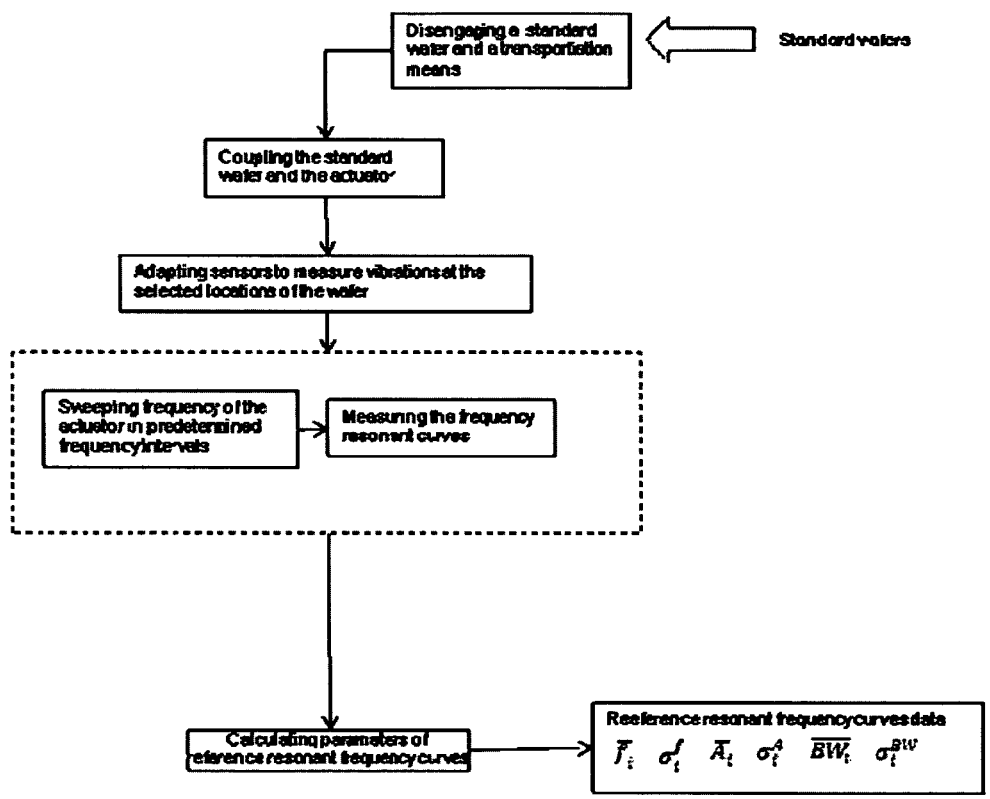
FIG. 12 is a flow-chart diagram of a calibration procedure according to the $12^{th}$ example of the invention.

FIG. 11 and FIG. 12 depict flow-chart diagrams and include procedures typically implemented in the invention.

Figure 13:
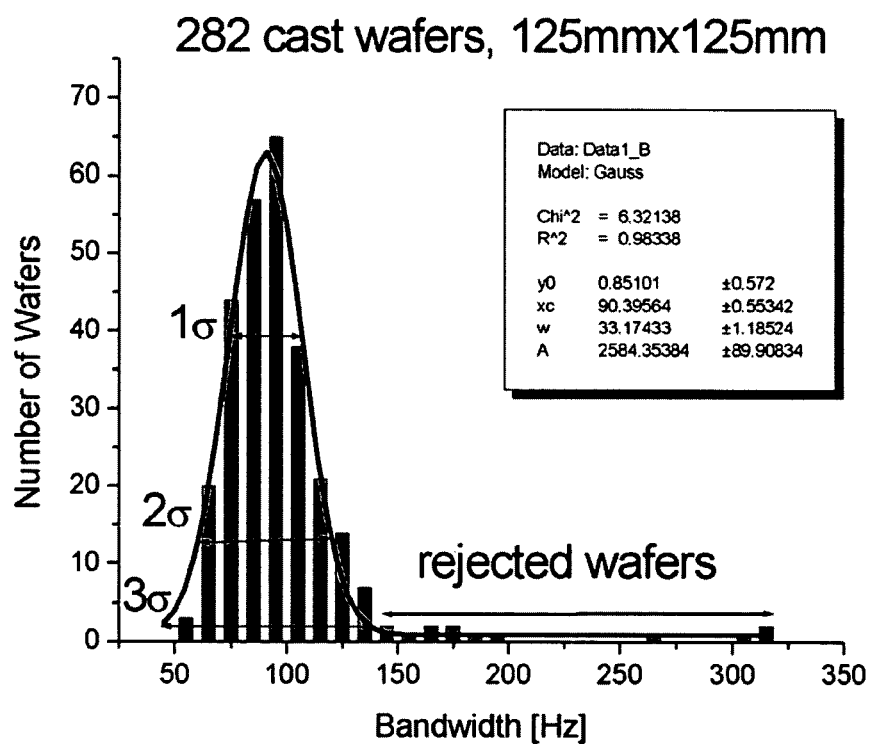
FIG. 13 is a histogram demonstrating a statistical distribution of bandwidths of a set of 282 125×125 mm wafers according to the $13^{th}$ example of the invention.
Figure 14:
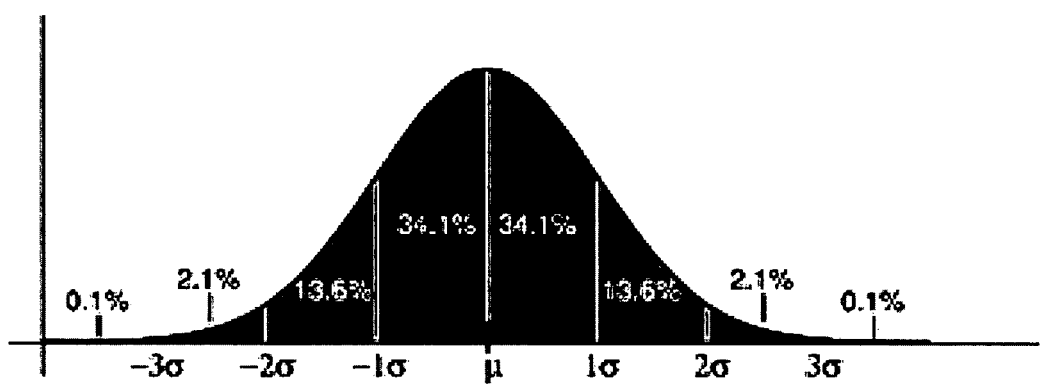
FIG. 14 depicts normal distribution of resonance frequency (a), bandwidth (b) and amplitude (c) according to the $14^{th}$ example of the invention.

With respect to FIG. 13 the histogram depicts statistical distribution of bandwidth of measured resonant frequency curves of a set of identical as-cut 286 cast wafers selected from a single batch. The distribution is approximated by Gaussian curve and has the following parameters: mean value–90.4 Hz, standard deviation–33 Hz. The wafers with bandwidth outside 3σ interval around the mean value were rejected FIG. 14 shows a normal distribution of one of rejection parameters of the method, i.e. the resonance frequency, the amplitude of the bandwidth on a set of standard wafers. Internal part of the normal distribution is less than one standard deviation (σ) from the mean (μ). For the normal distribution, this account for 68.2% of entire set of wafers, while two standard deviations (2σ) from the mean value account for 95.4% and three standard deviations account for 99.6%.

Figure 15:
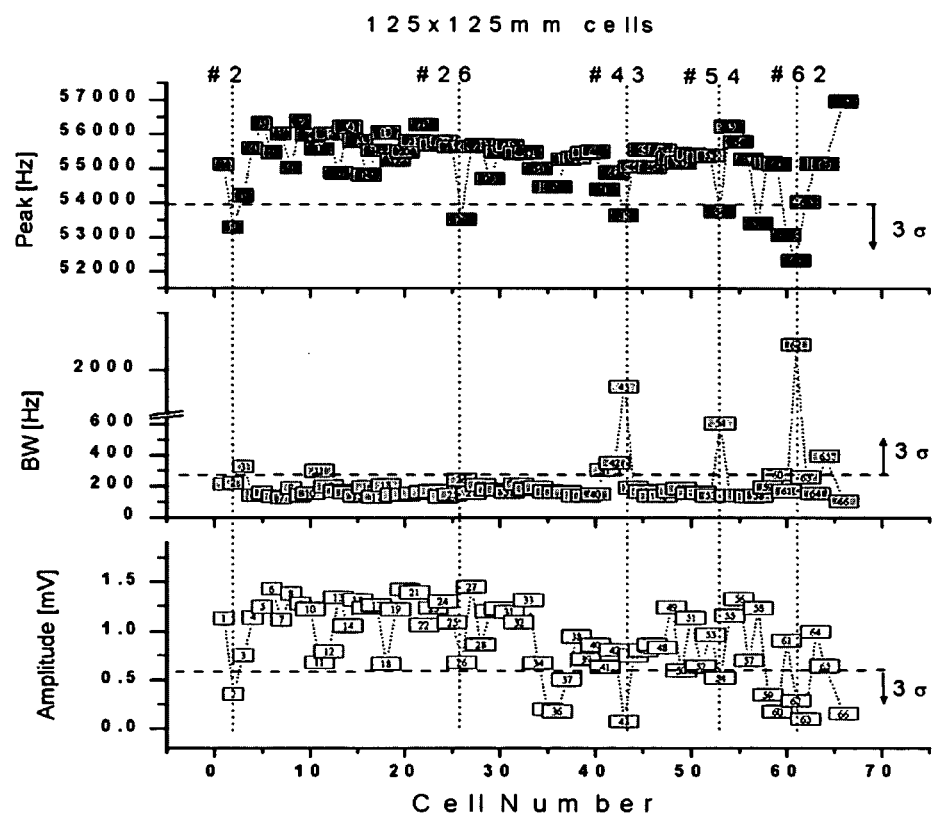
FIG. 15 demonstrates a statistical analysis performed on a set of 125 mm Si solar cell.

FIG. 15 demonstrates an importance of the simultaneous application of rejection criteria. Only cells which fall outside 3σ—thresholds for at least 2 of 3 rejection criterion were considered rejects. These cells (#2, 26, 43, 54 and 62) were independently measured using a Scanning Acoustic Microscope, which revealed cracks in the range of lengths from 3 mm to 50 mm.

The invention has been described in an illustrative manner and it is to be understood that the terminology that has been used is intended to be in the nature of words of description rather than of limitation. It is now apparent to those skilled in the art that many modifications and variations of the present invention are possible in light of the above teachings. It is, therefore, to be understood that the invention may be practiced otherwise than as specifically described.

The invention claimed is:

1. A method for testing for a crack in a wafer, comprising the steps of:
    coupling a broad-band actuator to the wafer;
    connecting a plurality of sweeping frequencies to the broad-band actuator for vibrating the wafer with sweeping frequencies within a plurality of independent frequency bands;
    coupling at least one acoustic sensor to the wafer for simultaneously measuring a measured peak frequency, a measured amplitude and a measured bandwidth of a resonant frequency curve of the vibrating wafer;
    comparing the measured peak frequency, the measured amplitude and the measured bandwidth of the resonant frequency curve of the vibrating wafer with a reference peak frequency, a reference amplitude and a reference bandwidth of a reference resonant frequency curve to determine a crack in the wafer; and
    rejecting the wafer in the event the wafer produces a change in any two of the measured peak frequency, the measured amplitude and the measured bandwidth of the resonant frequency curve relative to the reference frequency, the reference amplitude and the reference bandwidth of the reference resonant frequency curve.

2. A method for testing for a crack in a wafer as set forth in claim 1, wherein the step of coupling at least one acoustic sensor to the wafer includes coupling at least one acoustic sensor to a periphery of the wafer.

3. A method for testing for a crack in a wafer, comprising the steps of:
    coupling a broad-band actuator to the wafer;
    connecting a plurality of sweeping frequency generators to the broad-band actuator for vibrating the wafer with the plurality of sweeping frequencies within a plurality of independent frequency bands;
    coupling at least one acoustic sensor to the wafer for simultaneously measuring a measured peak frequency, a measured amplitude and a measured bandwidth of each of the plurality of resonant frequency curves of the vibrating wafer;
    comparing each of the plurality of measured peak frequency, the measured amplitude and the measured bandwidth of the plurality of resonant frequency curves of the vibrating wafer with a reference peak frequency, a reference amplitude and a reference bandwidth of a plurality of reference resonant frequency curves to determine a crack in the wafer; and rejecting the wafer in the event the wafer produces a change in any two of the measured peak frequency, the measured amplitude and the _measured bandwidth of the resonant frequency curve relative to the reference peak frequency, the reference amplitude and the reference bandwidth of the reference resonant frequency curve.

4. A method for in-line testing for a crack in wafers comprising the steps of:

transporting the wafers along a path;

coupling a broad-band actuator sequentially to a selected wafer;

connecting a plurality of sweeping frequency generators to the broad-hand actuator for vibrating the selected wafer with the plurality of sweeping frequencies within a plurality of independent frequency bands;

coupling at least one acoustic sensor to the selected wafer for simultaneously measuring a measured peak frequency, a measured amplitude and a measured bandwidth of each of the plurality of resonant frequency curves of the vibrating selected wafer;

comparing each of the plurality of measured peak frequency, the measured amplitude and the measured bandwidth of the plurality of resonant frequency curves of the vibrating selected wafer with a reference peak frequency, a reference amplitude and a reference bandwidth of a plurality of reference resonant frequency curves to determine a crack in the selected wafer; and rejecting the selected wafer when two of the measured peak frequency, the measured amplitude and the measured bandwidth of the plurality of resonant frequency curves of vibration of the selected wafer deviates from the reference peak frequency, the reference amplitude and the reference bandwidth of the plurality of reference frequency curves beyond a defined set of values, and decoupling the rejected selected wafer from the broad-band actuator and the acoustic sensor.

5. A method for in-line testing for a crack in wafers as set forth in claim 4, wherein the step of coupling at least one acoustic sensor to the water includes coupling at least one acoustic sensor to a periphery of the wafer.

6. A method for in-line testing for a crack in wafers as set forth in claim 4 wherein the step of rejecting the selected wafer includes disengaging the selected wafer from the path.

7. An apparatus for testing for a crack in a wafer, comprising:

a broad-band actuator;

a holder for coupling said broad-band actuator to the wafer;

a plurality of sweep frequency generator connected to said broad-band actuator for vibrating the wafer with the plurality of sweeping frequencies within a plurality of independent frequency bands;

an acoustic sensor coupled to the wafer for simultaneously measuring a measured peak frequency, a measured amplitude and a measured bandwidth of a resonant frequency curve of the vibrating wafer;

an electronic device for comparing said measured peak frequency, said measured amplitude and said measured bandwidth of said resonant frequency curve of the vibrating wafer with a reference peak frequency, a reference amplitude and a reference bandwidth of a reference resonant frequency curve to determine a crack in the wafer; and a rejector for rejecting the wafer in the event the wafer produces a change in any two of said measured peak frequency, said measured amplitude and said measured bandwidth of the resonant frequency curve relative to said reference peak frequency, said reference amplitude and said reference bandwidth of said reference resonant frequency curve.

8. An apparatus for testing for a crack in a wafer as set forth in claim 7, wherein said acoustic sensor is coupled to a periphery of the wafer.

9. An apparatus for testing for a crack in a wafer as set forth in claim 7, wherein said acoustic sensor is coupled to the wafer by a vacuum coupling.

10. An apparatus for testing for a crack in a wafer as set forth in claim 7, wherein said holder for coupling said broad-band actuator to the wafer includes said broad-band actuator mechanically supporting the wafer when said acoustic sensor is measuring said resonant frequency curve of the vibrating wafer.

11. An apparatus for testing for a crack in a wafer as set forth in claim 10, wherein said holder coupling said broad-band actuator to the wafer is located above the wafer.

12. An apparatus for testing for a crack in a wafer as set forth in claim 10, wherein said holder coupling said broad-band actuator to the wafer is located below the wafer.

13. An apparatus for testing for a crack in a wafer as set forth in claim 10, wherein said acoustic sensor includes at least two acoustic sensors for detecting mechanical vibrations at opposed locations on the wafer.

14. An apparatus for testing for a crack in a wafer, comprising:

a broad-band actuator;

a holder for coupling said broad-hand actuator to the wafer;

a generator subsystem comprising a plurality of generators timed to a plurality of independent frequency ranges connected to said broad-band actuator for vibrating the wafer with sweep frequencies within said plurality of independent frequency ranges;

an acoustic sensor coupled to the wafer for sensing a plurality of resonant frequency curves of the vibrating wafer in each of said plurality of independent frequency ranges:

an amplifier subsystem comprising a plurality amplifiers connected to said acoustic sensor for amplifying said plurality of resonant frequency curves in each of said plurality of independent frequency ranges;

an electronic device connected to said amplifier subsystem for comparing a measured peak frequency, a measured amplitude and a measured bandwidth of each of said plurality of resonant frequency curves in each of said plurality of independent frequency ranges of the vibrating wafer with a reference peak frequency, a reference amplitude and a reference bandwidth of a reference resonant frequency curve to determine a crack in the wafer; and a rejector for rejecting said cracked wafer.

15. An apparatus for in-line testing for a crack in wafers, comprising:

a transport for moving the wafers along a path;

a broad-band actuator;

a holder for coupling said broad-band actuator to a selected wafer;

a generator subsystem comprising a plurality of generators tuned to a plurality of independent frequency ranges connected to said broad-band actuator for vibrating said selected wafer with sweep frequencies within said plurality of independent frequency ranges;

an acoustic sensor coupled to the wafer for measuring a measure peak frequency, a measured amplitude and a measured bandwidth of a resonant frequency curve of the vibrating wafer in each of said plurality of independent frequency ranges;
an electronic device for comparing said measured peak frequency, the measure amplitude and the measured bandwidth of said resonant frequency curve of the vibrating wafer with a reference peak frequency, a reference amplitude and a reference bandwidth of a reference resonant frequency curve to determine a crack in the wafer;
a rejector for removing said selected wafer from said path when any two of said measured peak frequency, said measure amplitude and said measured bandwidth of said resonant frequency curve of said vibration of said selected wafer deviates from said reference peak frequency, said reference amplitude and said reference bandwidth of said reference resonant frequency curve beyond a defined set of values.

16. An apparatus for in-line testing for a crack in wafers as set forth in claim 15 wherein said sweep frequency generator excites mechanical vibrations in said selected wafer simultaneously in multiple predetermined frequency ranges.

17. An apparatus for in-line testing for a crack in wafers as set forth in claim 15, wherein said sweep frequency generator includes at least two electrical generators jointly delivering a superposition of the electrical signals to said acoustic actuator, and
said acoustic sensor comprising at least two electrical amplifiers each synchronized with a corresponding electrical generator and tuned to measure said vibrations of said selected wafer in one of a predetermined frequency ranges.

18. An apparatus for in-line testing for a crack in wafers as set forth in claim 15, wherein said acoustic sensor detects mechanical vibrations in said selected wafer and converting said vibrations into electrical signals.

19. An apparatus for in-line testing for a crack in wafers as set forth in claim 15, wherein said transport is a pick-and-place mechanism.

20. An apparatus for in-line testing for a crack in wafers as set forth in claim 15, wherein said transport is a conveyer belt.

* * * * *